United States Patent [19]

Mathiaparanam

[11] Patent Number: 5,218,127

[45] Date of Patent: Jun. 8, 1993

[54] METHOD OF PREPARING MONO (INDOLYLETHYLENYL) PHTHALIDES

[75] Inventor: Ponnampalam Mathiaparanam, Appleton, Wis.

[73] Assignee: Appleton Papers Inc., Appleton, Wis.

[21] Appl. No.: 972,407

[22] Filed: Nov. 6, 1992

Related U.S. Application Data

[63] Continuation of Ser. No. 817,263, Jan. 3, 1992.

[51] Int. Cl.$^5$ .......................................... C07D 405/14
[52] U.S. Cl. ................................................ 548/456
[58] Field of Search ........................................ 548/456

[56] References Cited

U.S. PATENT DOCUMENTS 4,119,776 10/1978 Farber ..................... 548/456

Primary Examiner—Robert W. Ramsuer
Attorney, Agent, or Firm—Benjamin Mieliulis

[57] ABSTRACT

Preparation of novel mono(indolylethylenyl) phthalides is disclosed. Specifically, these compounds are chromogenic mono(indolylethylenyl)phthalides of the formula

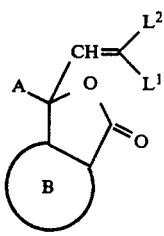

wherein A is as hereinafter defined and selected from moieties of the type

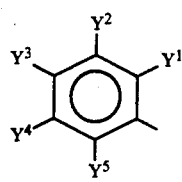

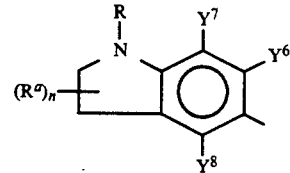

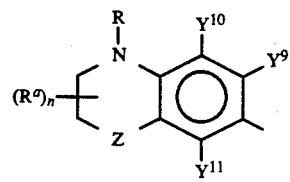

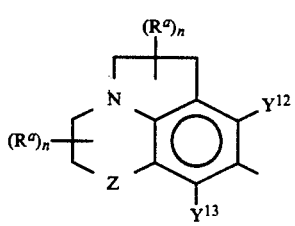

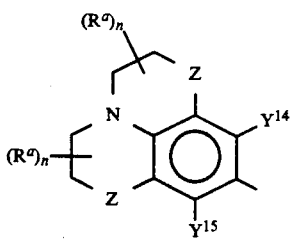

wherein L is an indole moiety as hereinafter defined; wherein B is a moiety of the type

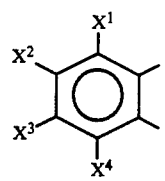

as hereinafter defined. The process disclosed comprises condensing indolylethylene with a keto acid or its derivative and an electron acceptor in an organic solvent.

6 Claims, 2 Drawing Sheets

METHOD OF PREPARING MONO (INDOLYLETHYLENYL) PHTHALIDES

This application is a continuation of Ser. No. 817,263 filed Jan. 3, 1992, now pending.

FIELD OF THE INVENTION

Background of the Invention

This invention relates to chromogenic mono(indolylethylenyl)phthalides (I) and methods for their production. More particularly, this invention relates to chromogenic compounds that are colorless or light-colored initially but provide intense colors when reacted with an electron accepting coreactant material; and, therefore, are eligible for use in pressure sensitive recording systems and thermal recording systems that can be read by a machine capable of reading in the wavelength range of 400 to 900 nm.

The chromogenic compounds of this kind also find use in photosensitive printing materials, typewriter ribbons, inks and the like. Imaging or printing in desired areas on support webs or sheets may be accomplished by effecting localized reactive contact between chromogenic material and an electron accepting material on or in such web or sheet, such material being brought thereto by transfer or originally there in situ. This selective reactive contact forms the colored prints or images in the intended areas.

The colorable chromogenic compounds of the invention can be combined with other chromogenic materials covering other or wider spectral ranges and can be used in pressure sensitive and thermal recording systems to provide images or prints which absorb over wider ranges of the electromagnetic spectrum. The commercial significance is that a larger assortment of available optical or near infrared readers can thus be effectively useful with record systems incorporating the chromogenic compounds of the invention.

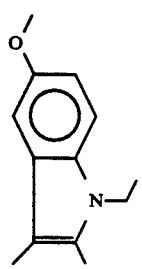

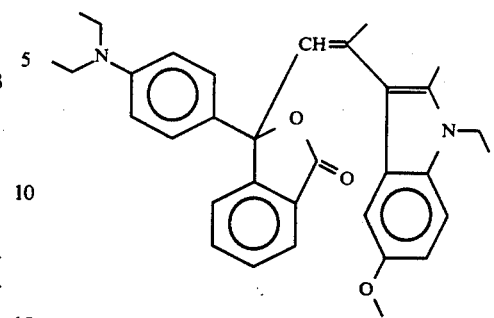

3-[1,1-bis(1-ethyl-5-methoxy-2-methylindole-3-yl)ethylene2-yl]-3-(4-diethylaminophenyl)phthalide.

Figure 2:
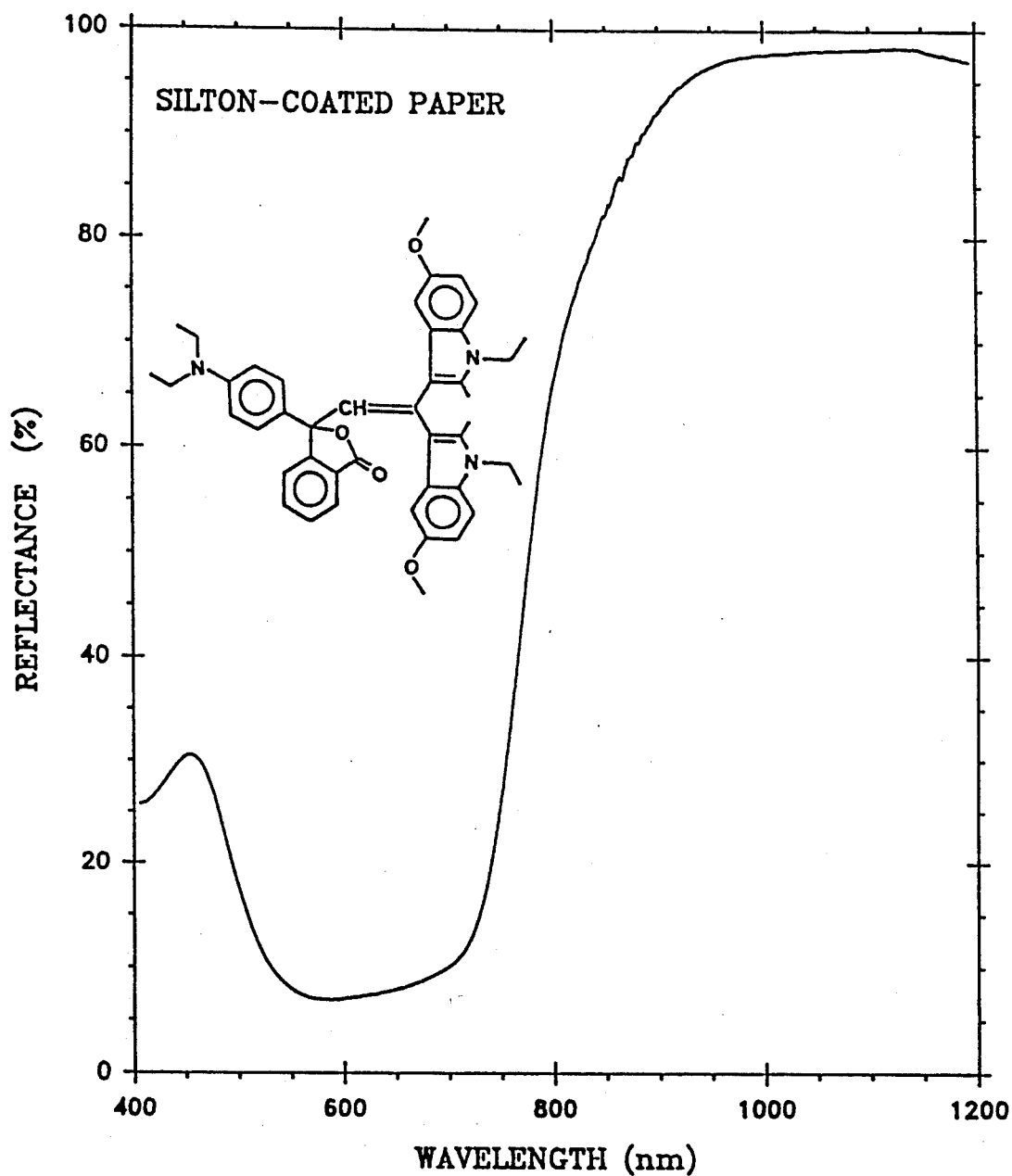

FIG. 2 is a graph of reflectance of the above compound when coated on silton-coated paper. Example details the synthesis of this compound.

DETAILED DESCRIPTION

The chromogenic compounds of this invention have the following general formula:

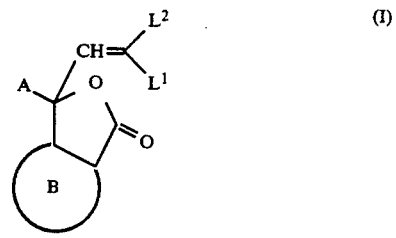

wherein A is independently selected from

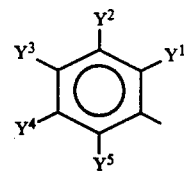

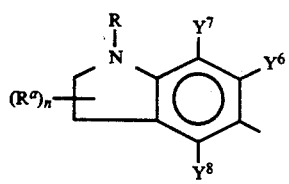

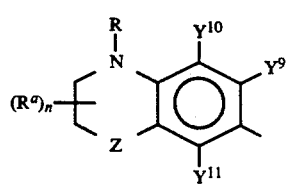

-continued

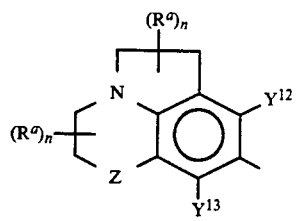

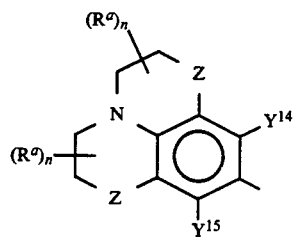

wherein $Y^3$ is independently selected from dialkylamino including symmetrical and unsymmetrical alkyl ($C_1$-$C_8$), alkylcycloalkylamino, dicycloalkylamino, alkylarylamino, diarylamino, dialkoxyalkylamino,

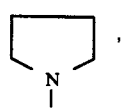

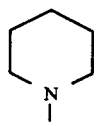

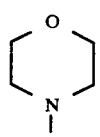

and

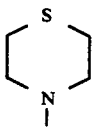

wherein each of $Y^1$, $Y^2$, $Y^4$-$Y^{15}$ is the same as $Y^3$ or independently selected from alkyl ($C_1$-$C_8$), alkoxy ($C_1$-$C_8$) or halogen;

wherein R is independently selected from alkyl ($C_1$-$C_8$), alkoxyalkyl, aryl (substituted or unsubstituted);

wherein Z is independently selected from $CH_2$, O, S, $SO_2$ or NR.

wherein each $R^a$ is independently selected from alkyl ($C_1$-$C_8$) and hydrogen;

wherein each n is an integer selected from 0 to four;

wherein B is independently selected from

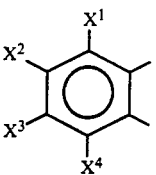

wherein each of $X^1$-$X^4$ is independently selected from hydrogen, halogen, alkyl ($C_1$-$C_8$), alkoxy ($C_1$-$C_8$), dialkylamino including symmetrical and unsymmetrical alkyl ($C_1$-$C_8$), alkylcycloalkylamino, dicycloalkylamino, alkylarylamino, diarylamino,

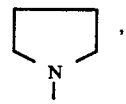

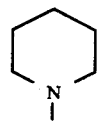

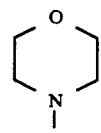

and

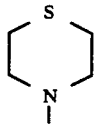

wherein each $L^1$ and $L^2$ is the same or different and is each independently selected from indole moieties (J1) through (J4) ($L^1$ need not be the same as $L^2$)

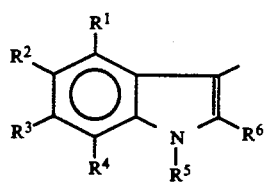
(J1)

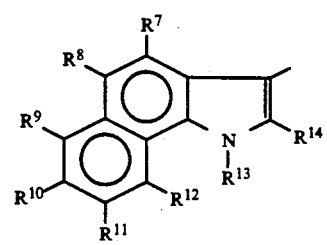
(J2)

-continued

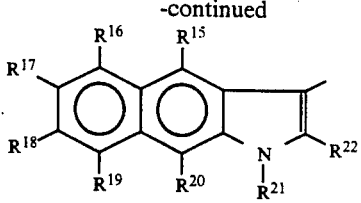
(J3)

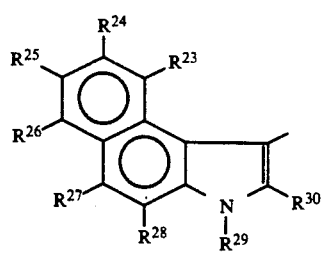
(J4)

wherein in (J1) through (J4) above each of $R^5$, $R^6$, $R^{13}$, $R^{14}$, $R^{21}$, $R^{22}$, $R^{29}$ and $R^{30}$ need not be the same and is each independently selected from hydrogen, alkyl ($C_1$–$C_8$), cycloalkyl, alkoxyalkyl, aroxyalkyl, substituted or unsubstituted aryl such as phenyl, naphthyl or heterocyclyl;

each of $R^1$, $R^2$, $R^3$, $R^4$, $R^7$, $R^8$, $R^9$, $R^{10}$, $R^{11}$, $R^{12}$, $R^{15}$, $R^{16}$, $R^{17}$, $R^{18}$, $R^{19}$, $R^{20}$, $R^{23}$, $R^{24}$, $R^{25}$, $R^{26}$, $R^{27}$ and $R^{28}$ need not be the same and is each independently selected from hydrogen, alkyl ($C_1$–$C_8$), cycloalkyl, substituted or unsubstituted aryl, halogen, alkoxy ($C_1$–$C_8$), aroxy, cycloalkoxy, dialkylamino including symmetrical and unsymmetrical alkyl ($C_1$–$C_8$), alkylcycloalkylamino, didcyloalkylamino, alkylarylamino, diarylamino,

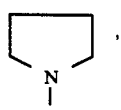,

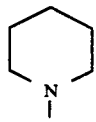,

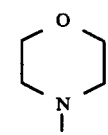, and

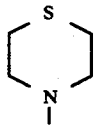.

Mono (indolylethylenyl)phthalides (I) were prepared by condensing indolylethylenes (II) with keto acids or their derivatives (III) using condensing agents (IV) (e.g. acid anhydrides, acid chlorides and Lewis acids) in an organic solvent.

Preferred examples of acid anhydrides and acid chlorides are acetic anhydride, propionic anhydride and acetyl chloride. Preferred Lewis acids are zinc chloride, boron trifluoride etherate, zinc chloride/phoxphoryl chloride and zinc chloride/thionyl chloride.

Since keto acids or their derivatives (III) undergo ring-chain tautomerism, they contain at least two reactive centers in either open or ring structure. Ring isomers can form derivatives not only from cyclic but also from acyclic structure, depending on the nature of reagents, temperature, solvent and substitution on (III). On the other hand, open or cyclic isomers may yield cyclic derivatives.

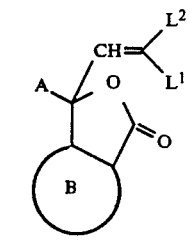 (I)

 (II)

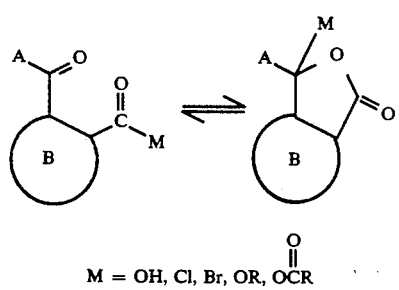 (III)

$M = OH, Cl, Br, OR, OCR$
               ‖
               O

In the following examples, general procedures for preparing certain mono(indolylethylenyl)phthalides of structure (I) are described; and the examples are not intended to be exhaustive and the moieties, as previously defined, are all eligible for use in any combination in preparing the compounds. Unless otherwise noted, all measurements, percentages and parts are by weight and in the metric system.

Spectroscopic data was used to confirm structures of compounds synthesized.

EXAMPLES

Figure 1:
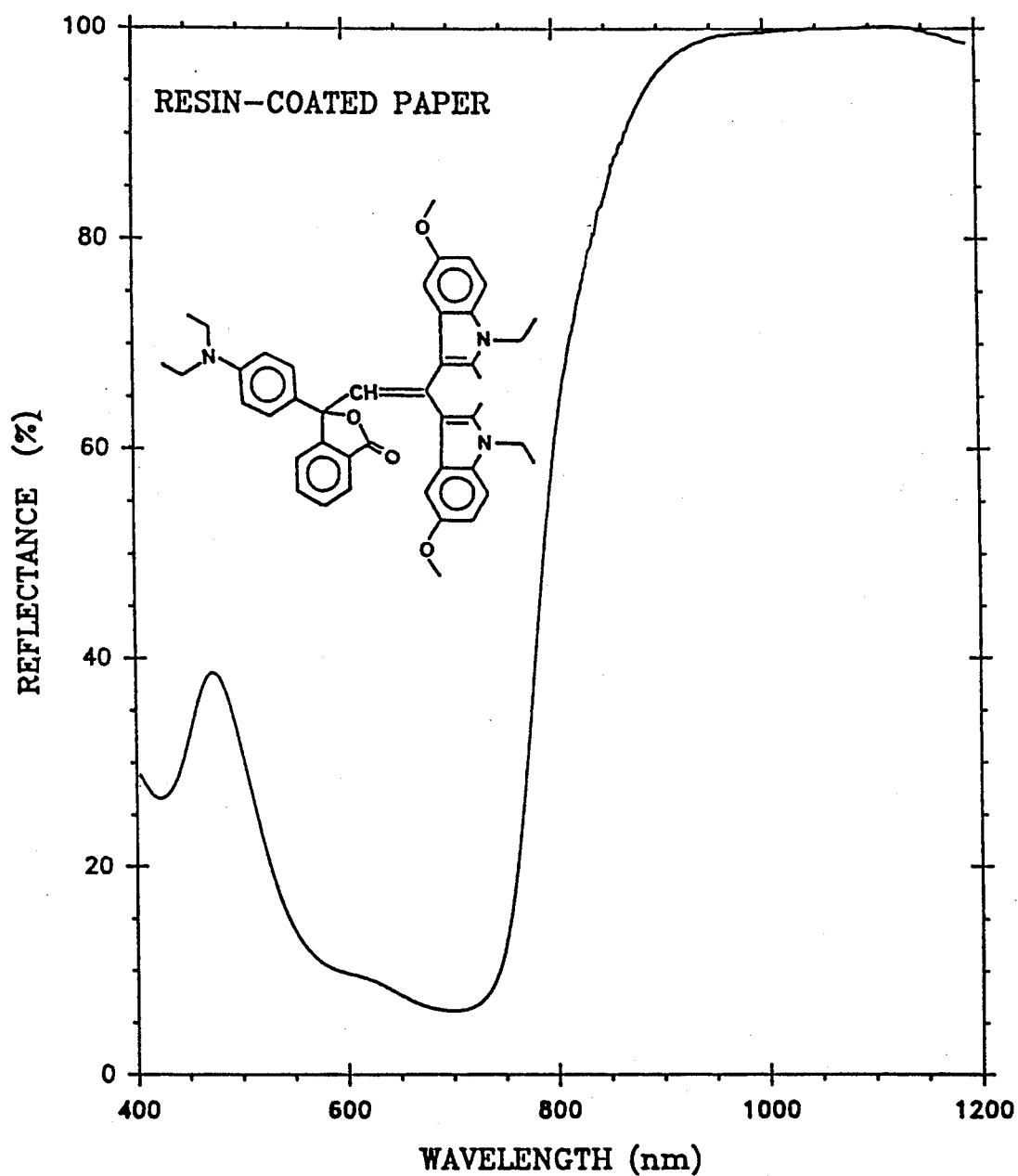
FIG. 1 is a graph of reflectance (%) from 400 to 1200 nm of the following compound when coated on resin-coated paper.

In the following examples, general procedures for preparing certain mono(indolylethylenyl)phthalides of structure (I) are described; and the examples are not intended to be exhaustive and the moieties, as previously defined, are all eligible for use in any combination in preparing the compounds. Unless otherwise noted, all measurements, percentages and parts are by weight and in the metric system. In Table 1, "sh" refers to a shoulder in the absorption spectra. As an illustration, in FIG. 1 there is a shoulder at 570 nm.

Satisfactory spectroscopic data were obtained for new compounds synthesized.

EXAMPLE 1

Preparation of 3-[1,1-bis(1-ethyl-5-methoxy-2-methylindole-3-yl)-ethylene-2-yl]-3-(4-diethylaminophenyl)phthalide (TABLE 1, ENTRY 1)

2-(4-Diethylaminobenzoyl)benzoic acid (3.0 g, 0.01 mole) and 1,1-bis(1-ethyl-5-methoxy-2-methylindole-3-yl)ethylene (4.0 g, 0.01 mole) in 1,2-dichloroethane (20 ml) and acetic anhydride (20 ml) were heated at 100° C. (oil bath temperature) for 4 hours. The reaction mixture was cooled to room temperature; treated with ice, toluene and aqueous sodium hydroxide(10%); stirred at 60° C. for 30 minutes; toluene layer separated and the aqueous layer extracted twice with toluene. The toluene extracts were combined, washed twice with hot water, dried and concentrated. The residue was chromatographed on silica gel using toluene and toluene:acetone:: 4:1 as eluants. Fractions containing the blue band were collected, combined and concentrated. The residue was recrystallized from 1,2-dichloroethane/methanol. The product was obtained as a white solid, m.p.: 217°–219° C.; Yield: 5.5 g (81%).

A solution of this product gives a blue color to paper coated with a phenolic resin, with reflectance minima at 570(shoulder) and 703 nm; and a royal blue color to paper coated with silton clay, with reflectance minima as a broad band from 550 to 750 nm.

The calculated analysis for $C_{44}H_{47}N_3O_4$, the title compound, is C, 77.50%; H, 6.95%; N, 6.16%; and O, 9.39%. Found on analysis: C, 77.04%; H, 7.12%; and N, 5.97%.

EXAMPLE 2

Preparation of 3-[1,1-bis(i-ethyl-2-methylindole-3-yl)ethylene-2-yl]-3-(4-diethylaminophenyl)phthalide (TABLE 1, ENTRY 2)

2-(4-Diethylaminobenzoyl)benzoic acid (3.0g, 0.01 mole) and 1,1-bis(1-ethyl-2-methylindole-3-yl)ethylene (3.4 g, 0.01 mole) in 1,2-dichloroethane (20 ml) and boron trifluoride etherate (2 ml, 2.3g, 0.016 mole) were heated (oil bath temperature 1000° C.) with exclusion of moisture. After 10 hours, the reaction mixture was cooled to room temperature, stirred with dilute ammonium hydroxide and toluene for 10 minutes at 60° C. and the organic layer separated. The organic layer was washed with hot water, dried and concentrated and the resulting residue chromatographed on silica gel using toluene and toluene:acetone::4:1 as eluants. Fractions containing the blue band were collected, combined and concentrated and the residue was further purified by medium pressure liquid chromatography on silica gel. After recrystallization from toluene/hexane, the product was obtained as a pale yellow solid, m.p.: 124°–126° C. Yield: 4.5g (72%).

A solution of the product gives a blue color to paper coated with a phenolic resin, with reflectance minima at 570(shoulder) and 710 nm; and a royal blue color to paper coated with silton clay, with reflectance minima as a broad band from 550 to 750 nm.

The calculated analysis for $C_{42}H_{43}N_3O_2$, the title compound, is C, 81.13%; H, 6.97%; N, 6.76%; and O, 5.15%. Found on analysis: C, 80.8%; H, 7.27%; and N, 6.80%.

EXAMPLE 3

Preparation of 3-[1-(5-chloro-2,7-dimethyl-1-ethylindole-3-yl)-1-(1-ethyl-2,5,7-trimethylindole-3-yl)ethylene-2-yl]-3-(4-diethylaminophenyl) -6-dimethylaminophthalide (TABLE 1, ENTRY 3)

2-(4-Diethylaminobenzoyl)-5-dime-thylaminobenzoic acid (1.9 g,5.5 mmole) and 1-(5-chloro-2,7-dimethyl-1-ethylindole-3-yl)-1-(1-ethyl-2,5,7-trimethylindole-3-yl)ethylene (2.3 g,5.5 mmole) were mixed with glacial acetic acid (25 ml) and concentrated sulfuric acid (0.6 g,5.9 mmole) and the reaction mixture was stirred at 40° C. for 24 hours with exclusion of moisture. Then, the reaction mixture was cooled to room temperature and poured into excess aqueous sodium hydroxide (10%) and toluene (200 ml). After stirring at 40° C. for 30 minutes, the toluene layer was separated, washed with hot water, dried and concentrated. The residue was purified by column chromatography (silica gel), followed by medium pressure liquid chromatography on silica gel. After recrystallization from toluene/methanol the product was obtained as a bluish white solid, m.p.: 190°–193° C. Yield: 1.3 g (32%).

A solution of this product gives a blue color to paper coated with a phenolic resin, with reflectance minima at 540 (shoulder) and 719 nm; and a blue color to paper coated with silton clay, with reflectance minima at 647 and 700 (shoulder) nm.

The calculated analysis for $C_{47}H_{53}N_4O_2Cl$, the title compound, is C, 76.14%; H, 7.21%; N, 7.56%; 0, 4.32%; and Cl, 4.78%. Found on analysis: C, 75.77%; H, 7.16%; N, 7.63%; and Cl, 4.93%.

EXAMPLE 4

Preparation of 3-[1,1-bis(1-ethyl-2-methylindole-3-yl)ethylene-2-yl]-3-(4-dimethylaminophenyl)-4,5,6,7-tetrachlorophthalide (TABLE 1, ENTRY 6)

3-Acetoxy-3-(4-dimethylaminophenyl)-4,5,6,7-tetrachlorophthalide (4.5 g, 0.01 mole), 1,1-bis(1-ethyl-2-methylindole-3-yl)ethylene (3.4g, 0.01 mole) and zinc chloride (1.4 g, 0.01 mole) in 1,2-dichloroethane (40 ml) were refluxed with stirring in a moisture free atmosphere. After 10 hours, the reaction mixture was worked up as described in EXAMPLE 1. The crude product was heated in hexane and filtered. Yield: 3.2g (44%), pale yellow solid, m.p.: 211°–213° C.

A solution of the product gives a bluish green color to paper coated with a phenolic resin, with reflectance minima at 600 (shoulder) and 719 nm; and a royal blue color to paper coated with silton clay, with reflectance minima at 600 and 720(shoulder) nm.

The calculated analysis for $C_{40}H_{35}N_3O_2Cl_4$, the title compound, is C, 65.67%; H, 4.82%; N, 5.74%; 0, 4.37%; and Cl, 19.39%. Found on analysis: C, 65.60%; H, 5.10%; N, 5.58%; and Cl, 19.66%.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes can be made by those skilled in the art without departing from the spirit and scope of the invention.

TABLE 1

REFLECTANCE MINIMA AND COLOR OF MONO(INDOLYLETHYLENYL)PHTHALIDES ON RESIN-COATED AND SILTON-COATED PAPERS

| ENTRY | COMPOUND | REFLECTANCE MINIMA (nm)* AND COLOR ON RESIN-COATED | REFLECTANCE MINIMA (nm)* AND COLOR ON SILTON-COATED |
|---|---|---|---|
| 1. | [structure] | 570 (Sh) 703 Blue | 550–750 Broad Band Royal Blue |
| 2. | [structure] | 570 (Sh) 710 Blue | 550–750 Broad Band Royal Blue |
| 3. | [structure] | 540 (Sh) 719 Blue | 647 700 (Sh) Blue |

TABLE 1-continued

REFLECTANCE MINIMA AND COLOR OF MONO(INDOLYLETHYLENYL)PHTHALIDES

ON RESIN-COATED AND SILTON-COATED PAPERS

REFLECTANCE MINIMA (nm)* AND COLOR ON

| ENTRY | COMPOUND | RESIN-COATED | SILTON-COATED |
|---|---|---|---|
| 4. | | 570<br>682<br>825 (Sh)<br>Bluish Green | 572<br>700 (Sh)<br>Purple |
| 5. | | 565<br>702<br>Greyish Blue | 570<br>698<br>Blue |
| 6. | | 600 (Sh)<br>719<br>Green | 600<br>720 (Sh)<br>Blue |

TABLE 1-continued
REFLECTANCE MINIMA AND COLOR OF MONO(INDOLYLETHYLENYL)PHTHALIDES ON RESIN-COATED AND SILTON-COATED PAPERS

| ENTRY | COMPOUND | REFLECTANCE MINIMA (nm)* AND COLOR ON | |
|---|---|---|---|
| | | RESIN-COATED | SILTON-COATED |
| 7. | [structure] | 620 (Sh) 713 Bluish Green | 600 690 (Sh) Blue |
| 8. | [structure] | 610 (Sh) 690 (Sh) 762 Bluish Green | 620 (Sh) 700 (Sh) 758 Pale Green |
| 9. | [structure] | 590 (Sh) 740 Pale Blue | 600 (Sh) 741 Greenish Blue |
| 10. | [structure] | 610 (Sh) 720 Green | 600 (Sh) 696 Green |

*Only the reflectance minima above 500 nm are reported.
Sh = Shoulder, φ = Phenyl

What is claimed is:

1. A process for the manufacture of mono(indolyl-ethylenyl)phthalide comprising condensing an indolyl-ethylene with a keto acid and an electron acceptor selected from the group consisting of acid anhydride, acid chloride and Lewis Acid in the presence of an organic solvent.

2. The process according to claim 1 wherein the electron acceptor is selected from the group consisting of acetic anhydride, propionic anhydride, acetylchloride, zinc chloride, boron trifluoride etherate, phosphoryl chloride and thionyl chloride.

3. The process according to claim 2 wherein the electron acceptor is zinc chloride.

4. A process for the manufacture of mono(indolylethylenyl)phthalide of the formula:

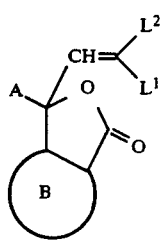

wherein A is independently selected from

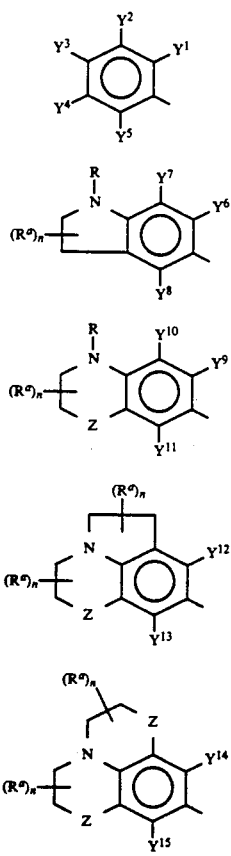

wherein $Y^3$ is independently selected form dialkylamino including symmetrical and unsymmetrical alkyl groups with one to eight carbons alkylcycloalkylamino, dicycloalkylamino, alkylarylamino, diarylamino, dialkoxyalkylamino,

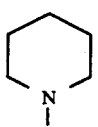

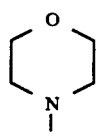

and

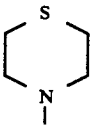

wherein each of $Y^1$, $Y^2$, $Y^4$-$Y^{15}$ is the same as $Y^3$ or independently selected from hydrogen, alkyl ($C_1$-$C_8$), alkoxy ($C_1$-$C_8$) and halogen;

wherein R is independently selected from alkyl ($C_1$-$C_8$), alkoxyalkyl, and aryl;

wherein Z is independently selected from $CH_2$, O, S, $SO_2$ or NR;

wherein each $R^a$ is independently selected from alkyl ($C_1$-$C_8$) and hydrogen;

wherein each n is an integer independently selected from O to four;

wherein B is

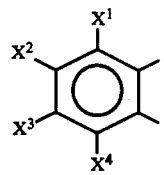

wherein each of $X^1$-$X^4$ is independently selected from hydrogen, halogen, alkyl ($C_1$-$C_8$), alkoxy ($C_1$-$C_8$), dialkylamino including symmetrical and unsymmetrical alkyl groups with one to eight carbons, alkylcycloalkylamino, dicycloalkylamino, alkylarylamino, diarylamino,

-continued

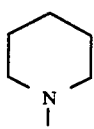

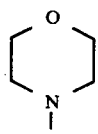

and

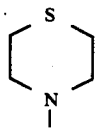

wherein each $L^1$ and $L^2$ is the same or different and is each independently selected from indole moieties (J1) through (J4);

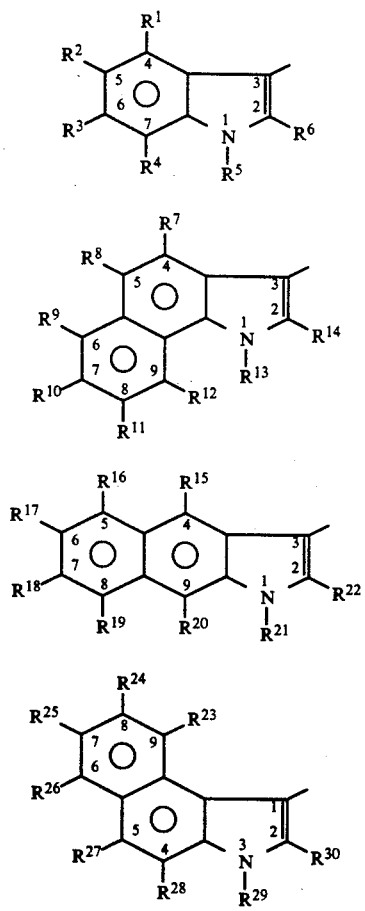

wherein in (J1) through (J4) each of $R^5$, $R^6$, $R^{13}$, $R^{14}$, $R^{21}$, $R^{22}$, $R^{29}$ and $R^{30}$ need not be the same and is each independently selected from hydrogen, alkyl ($C_1$-$C_8$), cycloalkyl, alkoxyalkyl, aroxyalkyl and aryl;

each of $R^1$, $R^2$, $R^3$, $R^4$, $R^7$, $R^8$, $R^9$, $R^{10}$, $R^{11}$, $R^{12}$, $R^{15}$, $R^{16}$, $R^{17}$, $R^{18}$, $R^{19}$, $R^{20}$, $R^{23}$, $R^{24}$, $R^{25}$, $R^{26}$, $R^{27}$ and $R^{28}$ is independently selected from hydrogen, alkyl ($C_1$-$C_8$), cycloalkyl, aryl, halogen, alkoxy ($C_1$-$C_8$), aroxy, cycloalkoxy, dialkylamino including symmetrical and unsymmetrical alkyl groups of one to eight carbons, alkylcycloalkylamino, dicycloalkylamino, alkylarylamino, diarylamino,

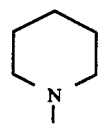

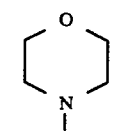

and

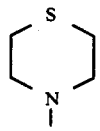

said process comprising condensing an indolylethylene with a keto acid or its derivative of formula (III i) or (III ii) and an electron acceptor selected from the group consisting of acid anhydride, acid chloride, and Lewis Acid in the presence of an organic solvent, said indolylethylene being of the formula

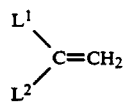

wherein each alkyl moiety herein is from one to eight carbons, each cycloalkyl moiety is from three to six carbons;

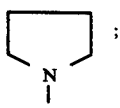

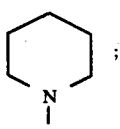

-continued

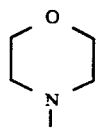

and

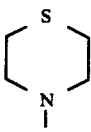

said keto acid or its derivative being of the formula selected from

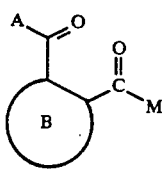 (III i)

or,

-continued

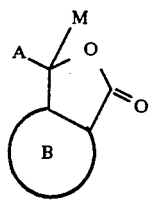 (III ii)

wherein A is as previously defined;
wherein B is as previously defined;
wherein M is selected from —OH, —Cl, —Br, —OR and

wherein R is alkyl ($C_1$–$C_8$).

5. The process according to claim 4 wherein the electron acceptor is selected from the group consisting of acetic anhydride, propionic anhydride, acetylchloride, zinc chloride, boron trifluoride etherate, phosphoryl chloride and thionyl chloride.

6. The process according to claim 5 wherein the electron acceptor is zinc chloride.

* * * * *